United States Patent [19]

Ginsburg

[11] Patent Number: 5,304,063
[45] Date of Patent: Apr. 19, 1994

[54] METHOD OF PRODUCING AND FITTING COMPLETE DENTURES

[76] Inventor: Stephen J. Ginsburg, 9 Everett St., Wellesley, Mass. 02181

[21] Appl. No.: 954,533

[22] Filed: Sep. 29, 1992

[51] Int. Cl.$^5$ .............................................. A61C 13/00
[52] U.S. Cl. ................................. 433/199.1; 433/167
[58] Field of Search ..................... 433/167, 171, 199.1, 433/215

[56] References Cited

U.S. PATENT DOCUMENTS

| | | | |
|---|---|---|---|
| 3,607,848 | 9/1971 | Stoy et al. | 433/199.1 X |
| 3,839,796 | 10/1974 | Hazar . | |
| 4,012,838 | 3/1977 | Abdenour . | |
| 4,017,971 | 4/1977 | Hazar . | |
| 4,019,253 | 4/1977 | Hazar . | |
| 4,097,992 | 7/1978 | Hazar . | |
| 4,161,065 | 7/1979 | Gigante | 433/35 |
| 4,175,322 | 11/1979 | Tureaud | 433/171 |
| 4,184,253 | 1/1980 | Tureaud | 433/171 |
| 4,361,528 | 11/1982 | Ginsburg et al. | 264/28 |
| 4,396,377 | 8/1983 | Roemer et al. | 433/199.1 |
| 4,398,007 | 8/1983 | Kubota et al. | 433/199.1 X |
| 4,615,665 | 10/1986 | Tateosian et al. | 425/16 |
| 4,711,913 | 12/1987 | Tateosian et al. | 522/14 |
| 4,863,977 | 9/1989 | Tateosian et al. | 522/14 |

OTHER PUBLICATIONS

TRIAD VLC System "Technique Manual and Operation/Service Manual" by Dentsply/York Division, pp. 14-17.

"Triad Technique Highlights" instructional leaflet by Dentsply/York Division (one page).

Article by Bobbie Beggs-Sargent "Denture systems cuts time, cost", The Dental Record, Fall 1989, Cover Page and pp. 2-3.

Primary Examiner—Gene Mancene
Assistant Examiner—Cindy A. Cherichetti
Attorney, Agent, or Firm—Krass & Young

[57] ABSTRACT

A thermally deformable denture base adapted to be fitted to an edentulous ridge and the surrounding tissue surfaces and a method of producing and fitting complete dentures incorporating the thermally deformable denture base. The denture base has an inner surface and an outer surface and is formed by a molding process from a doughy mixture of a plasticized liquid monomer and a methyl methacrylate polymer powder in a 1:3-3.5 ratio. When heated to a temperature above about 135° F., the denture base is malleable and may be molded in the mouth of a patient to attain an approximation of the tissue surfaces. The denture base may be incorporated into a complete denture by curing an unpolymerized resin material denture liner to the inner surface of the denture base and affixing teeth to the outer surface of the denture base.

11 Claims, 3 Drawing Sheets

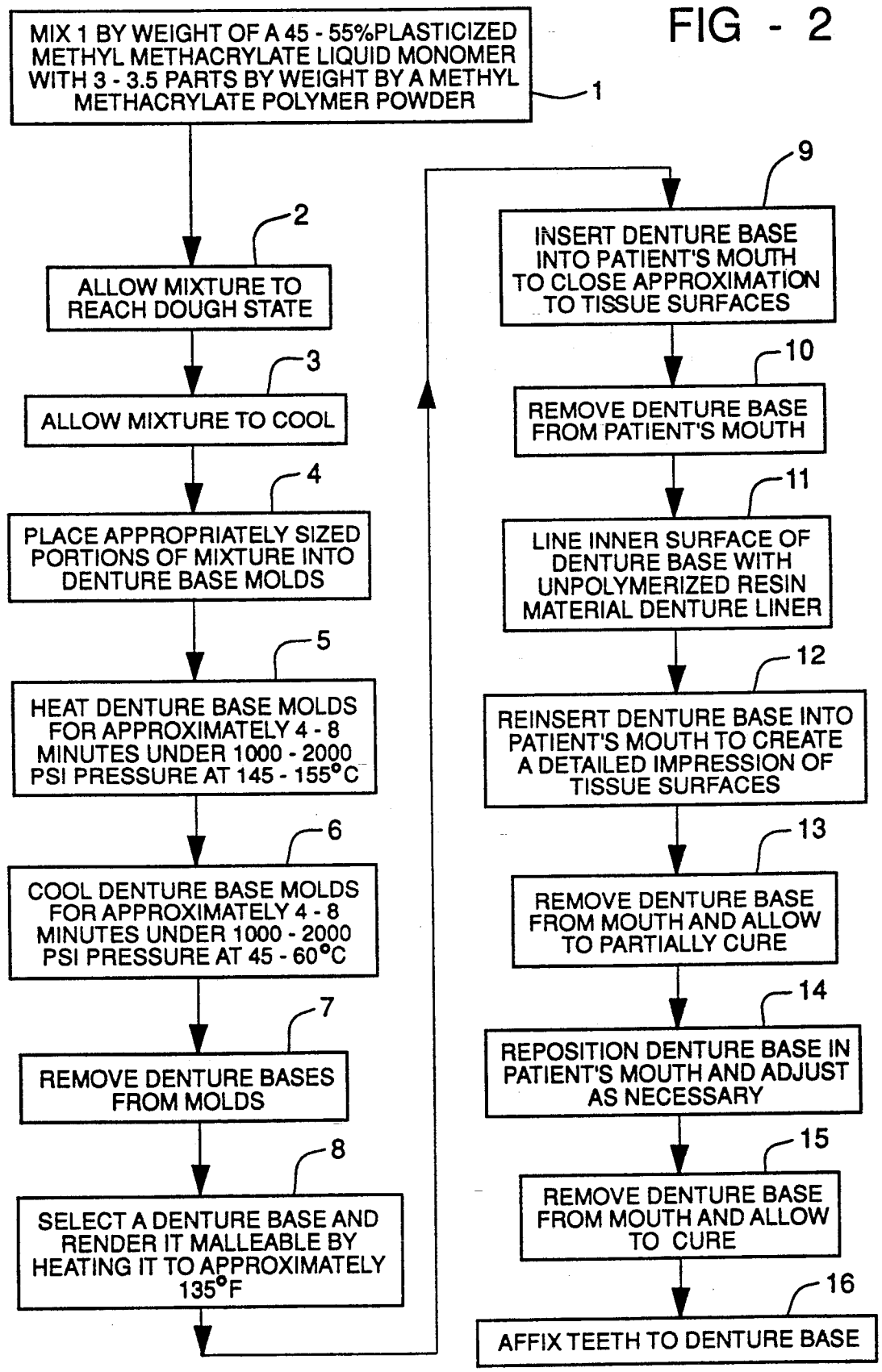

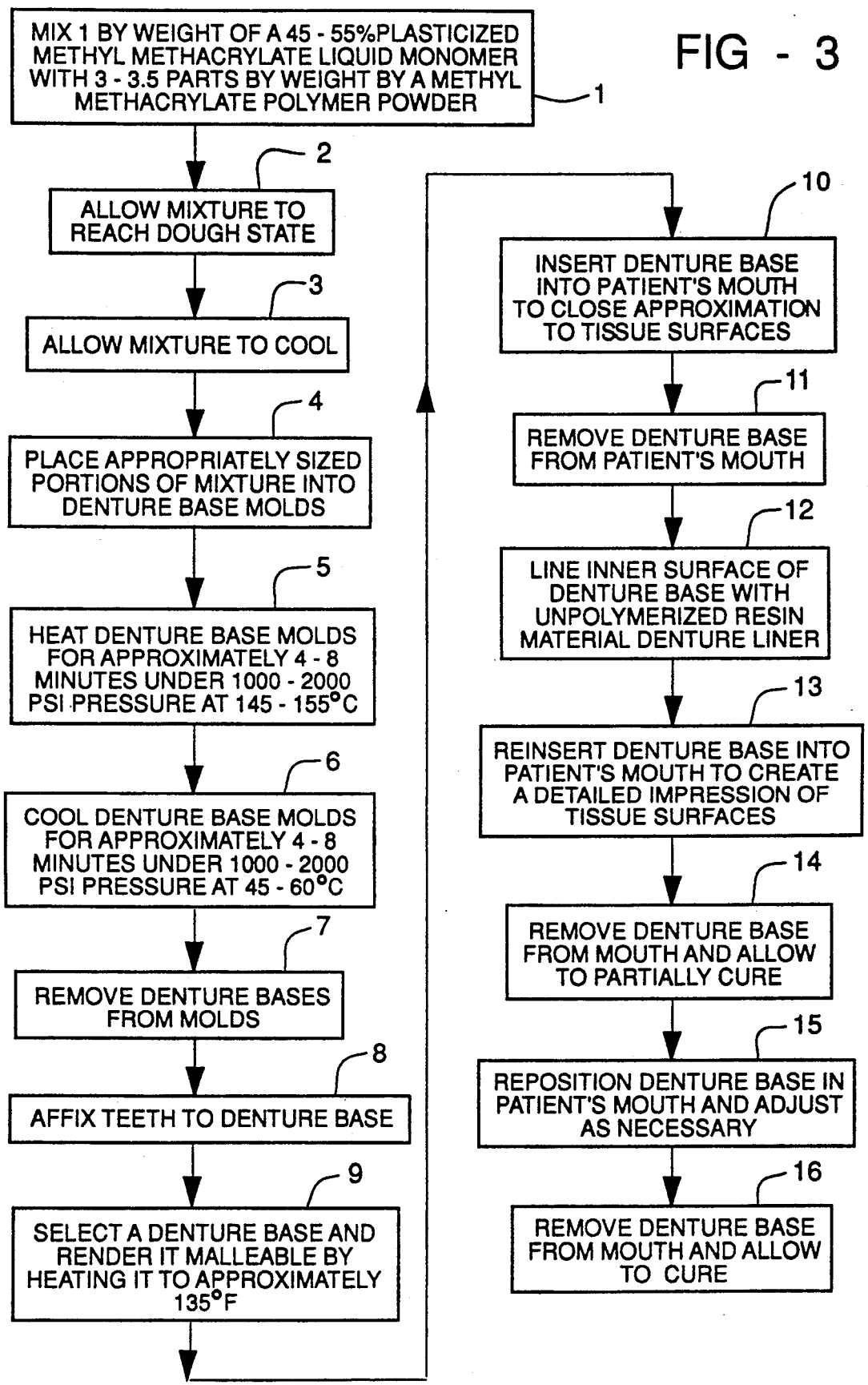

METHOD OF PRODUCING AND FITTING COMPLETE DENTURES

FIELD OF THE INVENTION

This invention relates generally to the field of dentures and more particularly to a thermally deformable denture base adapted to be fitted to an edentulous ridge and a method of producing and fitting complete dentures incorporating the base.

DESCRIPTION OF THE RELATED PRIOR ART

Molding and flasking methods and techniques for producing conventional dentures are well known in the prior art. However, the preparation of conventional customized dentures is an expensive, time-consuming process, requiring multiple visits to an experienced dentist and extensive preparation in a dental laboratory. Often, people forego obtaining conventional dentures for financial reasons, because they are physically unable to go to a dentist, or because they live in remote areas that do not have access to a qualified dentist.

Partially prefabricated or modular dentures are known in the prior art as economical substitutes for conventional dentures. Unlike conventional dentures, modular dentures utilize prefabricated components, e.g. prefabricated denture bases with imbedded teeth, to decrease both the number of visits to the dentist and the cost of making the denture. For example, U.S. Pat. No. 4,184,253 issued to Tureaud discloses a prosthetic preform comprised of a hard base into which the posterior prosthetic teeth are molded, with the anterior prosthetic teeth being mounted in a waxy material contained in cavities in the hard base.

Prefabricated modular denture components are typically manufactured in small, medium, and large sizes and provide a variety of different tooth shapes and colors to choose from. The modular denture eliminates several steps in the denture preparation and both time and money are saved by eliminating multiple visits to the dentist for precise measurements and repeated fittings.

Despite the economic advantages of a modular denture, the fit and aesthetic appearance of the modular denture is not always satisfactory to the wearer. For example, most modular dentures come with the teeth already positioned in the denture base. Depending on the selection available to the dentist, the color and shape of the teeth may not be optimal for the patient. In addition, due to the properties of the denture base material, the previously-imbedded teeth make positioning the modular denture on the patient's edentulous ridge difficult. Furthermore, the denture base material often has a tendency to revert back to its originally molded shape, destroying the fit and comfort of the modular denture and making customization difficult. U.S. Pat. No. 4,175,322 issued to Tureaud attempts to solve the latter problem by segmenting the denture base to allow for adjustment during fitting.

Accordingly, there is a need in the art for an economical denture base that is constructed of a material that has properties which enable it to be suitable for either (1) the satisfactory manipulation of previously-imbedded teeth without reverting back to its originally-molded shape or requiring segmentation of the base or (2) the affixation of a customized arrangement of teeth, thus providing the aesthetic benefits of a customized conventional denture without the inconvenience of numerous office visits and expense.

SUMMARY OF THE INVENTION

Disclosed and claimed herein is a thermally-deformable denture base configured to approximate an edentulous ridge and the surrounding interior contours of a patient's mouth. The inner surface of the denture base is adapted to be coated with a polymerizable liner to intimately conform to the details of the edentulous ridge and the surrounding tissues of the patient's mouth. The outer surface is adapted to support a rigid horseshoe of teeth. The denture base is formed by a dental molding process from a doughy mixture comprising 1 part by weight of a plasticized liquid monomer and 3-3.5 parts by weight of a methyl methacrylate polymer powder. The disclosed denture base material is deflectably deformable at a temperature above about 135° F. and enables the denture base to cure in a patient's mouth in an impression-taking position without distorting the impression recess upon removal from the mouth. The teeth may be affixed to the denture base either before or after the denture base has been finally fitted to the patient's mouth.

BRIEF DESCRIPTION OF THE DRAWINGS

FIG. 2 is a flow chart illustrating the steps in the method of producing the denture base of the present invention and incorporating the denture base into a complete modular denture; and FIG. 3 is a flow chart illustrating the steps in an alternate method of producing the denture base to a patient's mouth and incorporating the denture base into a complete modular denture.

DETAILED DESCRIPTION OF THE INVENTION

Figure 1:
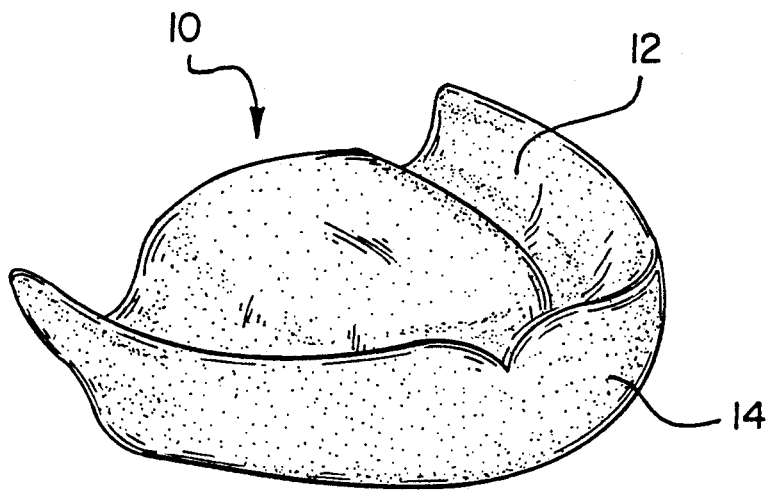
FIG. 1 is a front perspective view of a denture base configured to approximate an edentulous maxillary ridge.

Referring now to the drawings and, in particular to FIG. 1, there is shown a denture base 10 having an inner surface 12 and an outer surface 14. The denture base 10 is configured to approximate the edentulous ridge and the surrounding interior contours of the tissue surfaces of a patient's mouth. The inner surface 12 is adapted to be coated with a polymerizable liner to intimately conform to the details of the tissue surfaces so that the denture base accurately and comfortably fits the patient's mouth. The outer surface 14 of the denture base 10 is adapted to support a rigid horseshoe of teeth. The properties of the denture base 10 of the present invention are such that it is rendered malleable at approximately 135° F. thereby allowing the base to be molded in the mouth of a patient to attain an approximation of the tissue surfaces therein. Although the denture base 10 shown in FIG. 1 is for the maxillary edentulous ridge, it is understood that the present invention is equally applicable to a denture base for the mandibular edentulous ridge.

Referring now to FIG. 2, steps 1 through 7 of the flow chart illustrate the method of preparing the denture base mixture and molding the mixture in a standard-sized denture base mold to form the denture base 10. My U.S. Pat. No. 4,361,528, incorporated herein by reference, discloses a method of making a dental impression tray from a thermally-deformable material substantially identical to the material used in the present invention. However, unlike the denture base 10 of the present invention, the dental impression tray is used only in an intermediate step in the preparation of a complete denture; it is not part of the final permanent denture unit.

In step 1 of FIG. 2, one part by weight of a plasticized methyl methacrylate liquid monomer is mixed with 3–3.5 parts by weight of a methyl methacrylate polymer powder. In the preferred mixture, the plasticized methyl methacrylate liquid monomer is a mixture of 45–55% by weight of a methyl methacrylate liquid monomer and 45–55% by weight of a suitable liquid plasticizer such as diethyl phthalate. Also in the preferred mixture, the methyl methacrylate polymer powder has an average molecular weight of at least 650,000. Esschem Company, a Division of Sartomer Industries, Inc., P.O. Box 56, Essington, Pa. 19029 sells a suitable methyl methacrylate monomer as stock number 901 S 0000, a suitable plasticizer as stock number 927 S 0000, and a suitable methyl methacrylate polymer powder as Type 139 Standard Denture Polymer. In steps 2 and 3, the mixture is allowed to reach a doughy state and then to cool.

In steps 4 through 7, the doughy mixture is molded to approximate an edentulous ridge and the surrounding interior contours of an oral cavity. An appropriately sized portion of cooled doughy mixture is placed in each denture base mold. The denture base molds are then heated for approximately four to eight minutes at a temperature of 145°–155° C. and a pressure of 1000–2000 psi. After heating, the denture base molds are cooled for approximately four to eight minutes at a temperature of 45°–60° C. and a pressure of 1000–2000 psi. The cooled denture bases 10 are then removed from the molds.

In steps 8 through 16, the resultant molded denture base 10 is fitted to a patient's mouth and incorporated into a complete modular denture. The dentist selects an appropriately-sized denture base 10 and renders it malleable by heating it to approximately 135° F. by, for example, dipping the denture base 10 into a warm water bath. The warm denture base is then inserted into the patient's mouth and pressure is gently applied to attain a close approximation of the edentulous ridge and the surrounding interior contours of the oral cavity. After this initial fitting, the denture base is removed from the patient's mouth. The properties of the denture base material are such that the base 10 is able to maintain its fitted configuration after removal from the patient's mouth without reverting back to its originally molded shape.

Referring now to step 11 in FIG. 2, an unpolymerized resin material denture liner is provided to line the inner surface 12 of the denture base 10. The denture liner may be hardened through polymerization by any of a variety of methods including light, heat, or chemicals. The bonding of the denture liner to the hardened denture base 10 described herein sufficiently fixes the denture base 10 such that it is not distorted when the patient places hot foods or liquids in his or her mouth.

The denture liner is required to create and maintain a detailed intimate impression of the interior tissue surfaces of the patient's edentulous ridge and the surrounding interior contours of the mouth. To this end, the lined denture base is reinserted into the patient's mouth. The patient is guided into a proper centric position and the vertical dimensions of occlusion are checked. Pressure is applied to the lined denture base 10 and a detailed impression of the tissue surfaces is created. Upon removal from the patient's mouth, the liner is allowed to partially cure and, if necessary, the denture base 10 may be reinserted in the patient's mouth for additional adjustments. When the dentist and the patient are satisfied with the impression and fit of the denture base 10, the denture base liner is cured and hardened.

In the preferred method, a light-curing unpolymerized resin material is provided to line the denture base 10. Light-curable resins provide greater definition and give the practitioner infinite working time to perfect the fit of the liner. TRIAD ®, a light-curing resin material manufactured by Dentsply International Inc., 570 West College Ave., P.O. Box 872, York, Pa. 17405-0872, is particularly suited for lining the denture base 10 of the present invention. Details pertaining to the handling and curing of TRIAD ® are set forth in the literature commercially distributed with the product and in U.S. Pat. Nos. 4,711,913 and 4,863,977, all incorporated herein by reference.

The final step shown in FIG. 2 is the step of affixing the teeth to the outer surface 14 of the denture base 10. One method of affixing the teeth comprises the steps of applying wax to the outer surface 14 of the edentulous ridge of the denture base 10, positioning the selected teeth in the wax to fit the requirements of the patient, and replacing the wax with a hard bar of acrylic using a conventional dental flasking process.

In an alternative method, the teeth may be affixed to the denture base 10 by applying an unpolymerized resin material to the outer surface 14 of the edentulous ridge of the denture base 10, positioning the selected teeth in the unpolymerized resin to fit the requirements of the patient, and curing the resin material. Again, a light-curing resin material such as TRIAD ® is preferred for this step.

As set forth in FIG. 3, it is not necessary to affix the teeth after the denture base 10 has been fitted, lined, and cured. On the contrary, the teeth may be affixed to the denture base 10 prior to fitting the denture base 10 to the individual patient.

The steps shown in FIGS. 2 and 3 may be adapted for the preparation of either individual denture bases or large quantities of denture bases. For mass production purposes, the dimensions of the denture base molds may be varied to approximate the anticipated requirements of a particular population taking into account, for example, average heights and bone structures.

I claim:

1. A method of producing and fitting a modular denture from component parts, said method comprising the steps of:

providing a thermally-deformable denture base having an inner surface and an outer surface, said base configured to approximate the edentulous ridge and the surrounding interior contours of a patient's mouth, said base being made from a mixture comprising 1 part by weight of a plasticized liquid monomer and 3–3.5 parts by weight of a methyl methacrylate polymer powder;

heating the denture base to above about 135° F. to render said base malleable;

inserting the denture base in the patient's mouth and applying pressure to create a close approximation of the edentulous ridge and the surrounding interior contours of the patient's mouth in the denture base;

removing the denture base from the patient's mouth;

conforming an unpolymerized resin material denture liner to the inner surface of the denture base;
inserting the lined denture base in the patient's mouth and applying pressure to create a final detailed impression of the edentulous ridge and the surrounding interior contours of the patient's mouth;
removing the denture base from the patient's mouth;
curing the lined denture base so as to polymerize the liner;
affixing teeth to the outer surface of the denture base.

2. The method of claim 1 wherein the plasticized liquid monomer comprises a mixture of 45-55% by weight of methyl methacrylate liquid monomer and 45-55% by weight of a suitable liquid plasticizer.

3. The method of claim 1 wherein the methyl methacrylate polymer powder has an average molecular weight of at least 650,000.

4. The method of claim 1 wherein the step of affixing teeth comprises:
applying wax to the outer surface of the edentulous ridge of the denture base;
positioning said teeth in said wax to fit the requirements of the patient; and
replacing the wax with a hard bar of acrylic using a conventional dental flasking process.

5. The method of claim 1 wherein the step of affixing teeth comprises:
applying an unpolymerized resin material to the portion of the outer surface of the denture base which approximates the patient's edentulous ridge;
positioning the teeth in the unpolymerized resin material to fit the requirements of the patient; and
curing the resin material.

6. A method of making a modular denture, said method comprising the steps of:
(1) providing a thermally-deformable denture base having an inner surface and an outer surface, said base configured to approximate the edentulous ridge and the surrounding interior contours of a patient's mouth, the method of making said denture base comprising the steps of:
 (a) mixing 45-55% by weight of a methyl methacrylate liquid monomer and 45-55% by weight of a suitable liquid plasticizer to form a plasticized liquid monomer;
 (b) mixing said plasticized liquid monomer with methyl methacrylate polymer powder in a ratio of 1:3-3.5 parts by weight to form a mixture;
 (c) allowing the mixture to reach a doughy-like state;
 (d) placing said mixture into a mold conforming to the desired structure of the denture base;
 (e) heating the mold at a temperature of about 145°-155° C. for about 4-8 minutes under pressure of about 1000-2000 p.s.i. to provide a denture base;
(2) heating the denture base to above about 135° F. to render it malleable by dipping the denture base in warm water;
(3) inserting the denture base in the patient's mouth and applying pressure to create a close approximation of the edentulous ridge and the surrounding interior contours of the patient's mouth in the denture base;
(4) removing the denture base from the patient's mouth;
(5) conforming an unpolymerized resin material denture liner against the inner surface of the denture base;
(6) inserting the lined denture base in the patient's mouth and applying pressure to create a final detailed impression of the edentulous ridge and the surrounding interior contours of the patient's mouth;
(7) curing the lined denture base so as to polymerize the liner; and
(8) affixing teeth to the outer surface of the denture base.

7. A method of producing and fitting a modular denture from component parts, said method comprising the steps of:
providing a thermally-deformable denture base having an inner surface and an outer surface, said base configured to approximate the edentulous ridge and the surrounding interior contours of a patient's mouth, said base being made from a mixture comprising 1 part by weight of a plasticized liquid monomer and 3-3.5 parts by weight of a methyl methacrylate polymer powder;
affixing teeth to the outer surface of the denture base;
heating the denture base to above about 135° F. to render said base malleable;
inserting the denture base in the patient's mouth and applying pressure to create a close approximation of the edentulous ridge and the surrounding interior contours of the patient's mouth in the denture base;
removing the denture base from the patient's mouth;
conforming an unpolymerized resin material denture liner to the inner surface of the denture base;
inserting the lined denture base in the patient's mouth and applying pressure to create a final detailed impression of the edentulous ridge and the surrounding interior contours of the patient's mouth;
removing the denture base from the patient's mouth; and
curing the lined denture base so as to polymerize the liner.

8. The method of claim 7 wherein the plasticized liquid monomer comprises a mixture of 45-55% by weight of methyl methacrylate liquid monomer and 45-55% by weight of a suitable liquid plasticizer.

9. The method of claim 7 wherein the methyl methacrylate polymer powder has an average molecular weight of at least 650,000.

10. The method of claim 7 wherein the step of affixing teeth comprises:
applying wax to the outer surface of the edentulous ridge of the denture base;
positioning said teeth in said wax to fit the requirements of the patient; and
replacing the wax with a hard bar of acrylic using a conventional dental flasking process.

11. The method of claim 7 wherein the step of affixing teeth comprises:
applying an unpolymerized resin material to the portion of the outer surface of the denture base which approximates the patient's edentulous ridge;
positioning the teeth in the unpolymerized resin material to generally conform to patient edentulous ridge form, spatial relationships, and anatomic landmarks; and
curing the resin material.

* * * * *